US007524998B2

(12) United States Patent
Fukushima et al.

(10) Patent No.: US 7,524,998 B2
(45) Date of Patent: Apr. 28, 2009

(54) FABRICATION OF SELF-ASSEMBLED DENDRON MONOLAYERS

(75) Inventors: Hitoshi Fukushima, Tokyo (JP); Satoshi Nebashi, Tokyo (JP); Masaya Ishida, Cambridge (GB); Wilhelm J S Huck, Cambridge (GB); Andrew B Holmes, Melbourne (AU); Christine K Luscombe, Cambridge (GB)

(73) Assignees: Seiko Epson Corporation, Tokyo (JP); Cambridge University Technical Service, Ltd., Cambridge (GB)

( * ) Notice: Subject to any disclaimer, the term of this patent is extended or adjusted under 35 U.S.C. 154(b) by 698 days.

(21) Appl. No.: 11/170,057

(22) Filed: Jun. 30, 2005

(65) Prior Publication Data

US 2006/0008678 A1 Jan. 12, 2006

(30) Foreign Application Priority Data

Jul. 7, 2004 (GB) ................................. 0415243.5

(51) Int. Cl.
*C07C 22/08* (2006.01)
*C07C 22/04* (2006.01)
*C07C 22/02* (2006.01)
*C07C 22/00* (2006.01)
*B32B 9/04* (2006.01)
*B32B 17/06* (2006.01)
*B32B 17/00* (2006.01)

(52) U.S. Cl. .................... 570/129; 428/411.1; 428/426; 428/688; 428/689; 570/123; 570/124; 570/127; 570/130; 977/754

(58) Field of Classification Search .............. 428/411.1, 428/426, 688, 689; 570/123, 124, 127, 129, 570/130; 977/754
See application file for complete search history.

(56) References Cited

U.S. PATENT DOCUMENTS

| 6,312,809 | B1* | 11/2001 | Crooks et al. ............ 428/411.1 |
| 6,652,779 | B1 | 11/2003 | Zhang et al. |
| 2002/0197879 | A1* | 12/2002 | Fukushima et al. ......... 438/758 |
| 2003/0036215 | A1* | 2/2003 | Reid ........................... 438/52 |
| 2004/0012061 | A1* | 1/2004 | Reid et al. .................. 257/415 |
| 2004/0062927 | A1 | 4/2004 | Percec |

FOREIGN PATENT DOCUMENTS

| JP | A 9-274117 | 10/1997 |
| WO | WO-02066530 A1 * | 8/2002 |
| WO | WO 02/077037 A3 | 10/2002 |

OTHER PUBLICATIONS

Convergent Dendrons and Dendrimers: from Synthesis to Applications Grayson, S.M. and Frechet, J.M.J. Chem. Rev., 101, 12, 3819-3868, 2001, 10.1021/cr990116h.*
Application of Isomorphous Replacement in the Structure Determination of a Cubic Liquid Crystal Phase and Location of Counterions Dukeson, D.R., Ungar, G., Balagurusamy, V.S.K., Percec, V., Johansson, G.A., and Glodde, M. J. Am. Chem. Soc., 125, 51, 15974-15980, 2003, 10.1021/ja037380j.*
Fluorescent Conjugated Dendrimers with Fluorinated Terminal Groups: Nanofiber Formation and Electroluminescence Properties Zhao, Zujin, Li, Juo-Hao, Chen, Xiaopeng, Lu, Ping, and Yang, Yang Org. Lett., 2008, 10.1021/ol801001h.*
New Accelerated Strategy for the Synthesis of Poly(Ether Ketone) Dendrons Abramov, M.A., Shukla, R., Amabilino, D.B., and Dehaen, W. J. Org. Chem., 67, 3, 1004-1007, 2002, 10.1021/jo015805j.*
Fluorophobic Effect Induces the Self-Assembly of Semifluorinated Tapered Monodendrons Containing Crown Ethers into Supramolecular Columnar Dendrimers Which Exhibit a Homeotropic Hexagonal Columnar Liquid Crystalline Phase Percec, V., Johansson, G., Ungar, G., and Zhou, J. J. Am. Chem. Soc., 118, 41, 9855-9866, 1996, 10.1021/ja9615738.*
Nanoscale Architectural Control and Macromolecular Engineering of Nonlinear Optical Dendrimers and Polymers for Electro-Optics Luo, J., Haller, M., Ma, H., Liu, S., Kim, T.-D., Tian, Y., Chen, B., Jang, S.-H., Dalton, L.R., and Jen, A.K-Y. J. Phys. Chem. B, 108, 25, 8523-8530, 2004, 10.1021/jp036714o.*
Synthesis, Characterization, and Derivatization of Hyperbranched Polyfluorinated Polymers Mueller, A., Kowalewski, T., and Wooley, K.L. Macromolecules, 31, 3, 776-786, 1998, 10.1021/ma971201z.*
Synthesis of Supercritical Carbon Dioxide Soluble Perfluorinated Dendrons for Surface Modification Luscombe, C.K., Proemmel, S., Huck, W.T.S., Holmes, A.B., and Fukushima, H. J. Org. Chem., 72, 15, 5505-5513, 2007, 10.1021/jo070293f.*
Zhang et al., "Investigation into Self-Assembled Monolayers of a Polyether Dendron Thiol: Chemisorption, Kinetics, and Patterned Surface," American Chemical Society, Langmuir, 16, pp. 3813-3817, 2000.
Zhang et al., "Self-assembled monolayers of new dendron-thios: manipulation of the patterned surface and wetting properties," The Royal Society of Chemistry, Chem. Commun. pp. 1906-1907, 2001.
Bo et al., "Self-assembled Monolayers of Dendron-thiol on Solid Substrate," The Chemical Society of Japan, Chemistry Letters, pp. 1197-1998, 1998.

* cited by examiner

*Primary Examiner*—Callie E Shosho
*Assistant Examiner*—John Freeman
(74) *Attorney, Agent, or Firm*—Oliff & Berridge, PLC

(57) ABSTRACT

A dendron (2) comprising a focal point (4) and a plurality of fluorinated end groups (9) is disclosed, including one having a thiol, a silane, a carboxylic acid, a phosphonate or another moiety at the focal point suitable for chemisorption to a substrate (3). A self-assembled monolayer comprising a plurality of dendrons bonded to a substrate and a device comprising the self-assembled monolayer are also disclosed.

27 Claims, 3 Drawing Sheets

FABRICATION OF SELF-ASSEMBLED DENDRON MONOLAYERS

This application claims the benefit of Great Britain Patent Application No. 0415243.5, filed Jul. 7, 2004. The entire disclosure of the prior application is hereby incorporated by reference herein in its entirety.

The present invention relates to a method of fabricating self-assembled dendron monolayers onto a substrate and to products including such monolayers.

BACKGROUND OF THE INVENTION

Self-assembled monolayers (SAMs) have attracted much attention in areas such as device engineering because of the versatility they provide for surface modification. SAMs are highly ordered molecular assemblies that form spontaneously by chemisorption of functionalised molecules on a variety of substrates such as metals, Indium Tin Oxide (ITO), silicon, and glass. These molecules organise themselves laterally, most commonly via van der Waals interactions between long aliphatic chains. The principles and practice of deposition of monolayers are described in detail in a publication by A Ulman entitled "Introduction to Thin Organic Films: From Langmuir-Blodgett to Self-Assembly", published by Boston Academic Press, 1991. SAMs have found widespread research interest because of potential applications related to control over wettability, biocompatibility and corrosion resistance of surfaces.

For many electronic, optical and electro-optical devices for example, the ability to modify the properties of surface areas of the devices makes SAMs attractive for many applications, such as modification of surface hydrophobicity, packaging and electrical insulation. Furthermore, as SAMs exhibit excellent barrier properties, they are considered very appropriate for use as protective coatings on metal surfaces because they form thin highly crystalline barrier films. Gold has found widespread application and, for example, is used extensively in the electronics industry in integrated circuit technology. Also, as a relatively inert metal it has also been used as a protective layer in certain chemical environments, such as a liner material for the ink chambers in ink jet print heads. However, gold will dissolve under appropriate chemical or electrochemical conditions, so the ability of SAMs to provide a very thin protective layer to such metal layers in harsh chemical environments where metal layer corrosion is known to occur is also considered extremely attractive. However, SAMs have been found to exhibit certain drawbacks which, to date, have severely limited their commercial application in industrial processes.

To date, the SAM material is deposited by dissolving the material in an appropriate solvent and, as such, the monolayer formation over the required flat surface areas, which usually include surface discontinuities arising from design features dictated by the practical application of devices, is difficult to control. As the layers are self-aligning, they often exhibit molecular sized defects or holes in the layer. These defects can limit their use as barrier or passivation layers in certain industrial applications because the barrier properties provided by the densely packed molecules of the SAM material can be breached through the molecular sized defects.

Furthermore, although SAMs are typically in the order of only about 2 nm thickness, they are relatively slow to deposit. Typical deposition times range from several hours to a few days with the normal solvents used for the compounds. Heavily fluorinated compounds, such as thiols carrying aliphatic tails with multiple fluorine substituents, have been used to form hydrophobic SAMs on gold substrates. A measure for the hydrophobicity of a surface is the contact angle between a drop of water and that surface. These SAMs are quite robust and are stable up to 150° C. as described by Fukushima et al in The Journal of Physical Chemistry, B, (2000) 104, pages 7417 to 7423, so it can be appreciated that such monolayers could find widespread industrial application if the concerns associated with fabrication can be met.

Typically, SAM molecules comprise a head that is attracted to and bonds with the substrate material and a functionalised tail, such as an alkyl tail. Such single chain, linear perfluoroalkyl SAMs have been fabricated on metallic, glass and silicon type substrates. For metallic substrates, the head preferably comprises a thiol and for glass and silicon type substrates the head preferably comprises a silane.

In particular, for metallic substrates, which may consist of a layer of Au, Ag, Cu, Pd, Fe, Hg, GaAs, ITO, or $Fe_2O_3$ on a suitable supporting medium, the SAM may typically comprise a substance including semi-fluorinated, sulphur-containing compounds of the formula:

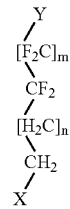

wherein X can be (but is not necessarily limited to) R—SH, RS—SR, or R—S—R (where R denotes the rest of the molecule). Preferably, X is a thiol.

The numbers m and n denote the number of fluorinated and non-fluorinated carbon atoms, respectively, and lie within the range of 1-20. Y preferably indicates a $CF_3$ functional group. Y may be further modified to incorporate one or more substituents such as vinyl, styryl, acryloyl, methacryloyl or alkyne for further functionalisation or cross-linking, with one or more spacer group such as $CH_2$ to facilitate attachment.

Self-assembled monolayers on glass, mica, $SiO_2$, $Al_2O_3$, or $Ga_2O_3$ typically involve semi-fluorinated silane derivatives of the formula:

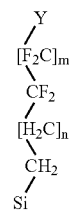

wherein Si can be (but is not necessarily limited to) $SiCl_3$, $Si(OCH_3)_3$, $Si(OCH_2CH_2CH_3)_3$, $Si(OCH_3)_2Cl$, or $Si(CH_2CH_3)_2Cl$. Preferably, Si is $SiCl_3$. The numbers m and n denote the number of fluorinated and non-fluorinated carbon atoms, respectively, and lie within the range of 1-20. Y preferably indicates a $CF_3$ functional group. Y may be further modified to incorporate one or more substituents such as vinyl, styryl, acryloyl, methacryloyl or alkyne for further functionalisation or cross-linking, with one or more spacer group such $CH_2$ to facilitate attachment.

Compressed carbon dioxide ($CO_2$) is known to be a clean and versatile solvent medium for a wide range of materials, including heavily fluorinated compounds. Supercritical $CO_2$ has been used for polymer synthesis and polymer processing. Such use is described in an article by A Cooper entitled "Polymer Synthesis and Processing using Supercritical Carbon Dioxide", published in The Journal of Materials Chemistry, 2000, 10, pages 207 to 234. A supercritical fluid may be defined as a substance for which both temperature and pressure are above the critical values for the substance and which has a density close to or higher than its critical density. For $CO_2$ the critical density is recognised to be 0.47 g cm$^{-3}$, and the critical temperature and pressure are recognised to be 31.1° C. and 73.8 bar. Compressed $CO_2$ has also been proposed as a solvent for the preparation of organic molecules, as described in a Special Issue of Chemical Review, 1999, 99 Volume 2.

Dendrimers are a type of regular-branched polymeric molecule. Their unusual structures can be precisely controlled at the molecular level and they have unique properties. In particular, they are spherical, have a single molecular weight and can be tailored to provide desired functions. A schematic view of a dendrimer 1 is shown in FIG. 1.

Dendrons are also regular-branched polymeric molecules and their structures can also be precisely controlled. However, they are wedge-shaped rather than spherical and comprise a focal point from which the branches originate. A schematic view of three dendrons 2 attached to a surface 3 is shown in FIG. 2. As shown in the figure, one chain extends from the focal point 4. The chain has two branches 5, 6 extending from it. Two further branches extend from each of the branches 5, 6 and so on. Each fork in a branch may be considered as the start of a different "layer" in the dendron. Thus, the dendrons 2 shown in FIG. 2 have five layers referenced 4, 5, 7, 8 and 9 respectively. Different dendrons may have different numbers of branches extending from each branch and different numbers of layers.

Dendron thiols, that is dendrons with a thiol group at the focal point are also known and have been considered as building blocks in nanotechnology.

SUMMARY OF THE INVENTION

According to the present invention, there is provided a dendron comprising a focal point and a plurality of fluorinated end groups.

Preferably, the dendron has a thiol, a silane, a carboxylic acid, a phosphonate or another moiety at the focal point suitable for chemisorption to a substrate.

The present invention comprises such dendrons of first, second and third generations and comprises dendrons having the structure of any of examples 1 to 7 discussed below.

According to another aspect of the present invention, there is provided a self-assembled monolayer comprising a plurality of dendrons of the present invention bonded to a substrate.

In a preferred embodiment, the substrate is a metal oxide or other oxide, such as silica or glass, and the plurality of dendrons includes dendrons having a silane as the focal point.

In another preferred embodiment, the substrate is a metal and the plurality of dendrons includes dendrons having a thiol as the focal point.

In one preferred embodiment, the monolayer is formed by exposure of the substrate to a solution of the dendron in dichloromethane and/or octafluorotoluene. Preferably, the concentration of the dendron in the solution is approximately 1 mM or more. Preferably, the substrate is exposed to the solution at a temperature of between approximately 10° C. and 65° C. and more preferably between approximately 10° C. and 25° C. Preferably, the substrate is exposed to the solution for between approximately 1 minute and 24 hours and, more preferably, for approximately 30 minutes or less.

In another preferred embodiment, the self-assembled monolayer is formed by exposure of the substrate to the dendron in compressed $CO_2$. Preferably, the $CO_2$ is supercritical $CO_2$. Preferably, the monolayer is formed by placing the substrate surface and the dendron in a sealed vessel, introducing $CO_2$ and discharging the $CO_2$ from the vessel and, more preferably, the $CO_2$ is introduced at a pressure of up to 1000 psi. It is also preferred that the steps of placing the substrate surface and the dendron in a sealed vessel, introducing $CO_2$ up to a pressure of 1000 psi and discharging the $CO_2$ from the vessel are repeated three or more times.

According to another aspect of the present invention, there is provided a device comprising a self-assembled monolayer of the present invention. Preferably, the device is a fluid deposition device and, more preferably, the device is an ink jet print head or an ink jet printer.

DESCRIPTION OF THE DRAWINGS

Embodiments of the present invention will now be described by way of further example only and with reference to the accompanying drawings, in which.

DETAILED DESCRIPTION

The inventors of the present invention have realised that an unexpectedly high degree of hydrophobicity can be achieved by forming a SAM of dendrons with fluorinated side-chains, which are hitherto unknown.

Accordingly, the inventors have produced a variety of such fluorinated dendrons and have further produced SAMs under different conditions using this variety of dendrons. Specifically, the SAMs were produced under a variety of temperatures and using a variety of solvents. In each case, it has been found that a surface with an unexpectedly high hydrophobicity is produced. Moreover, in some embodiments the SAMs have unexpectedly high and hitherto unknown degrees of chemical and thermal stability. This is evidenced by the high contact angles of water on the SAMs and by the ellipsometry thickness of the SAMs.

Figure 1:
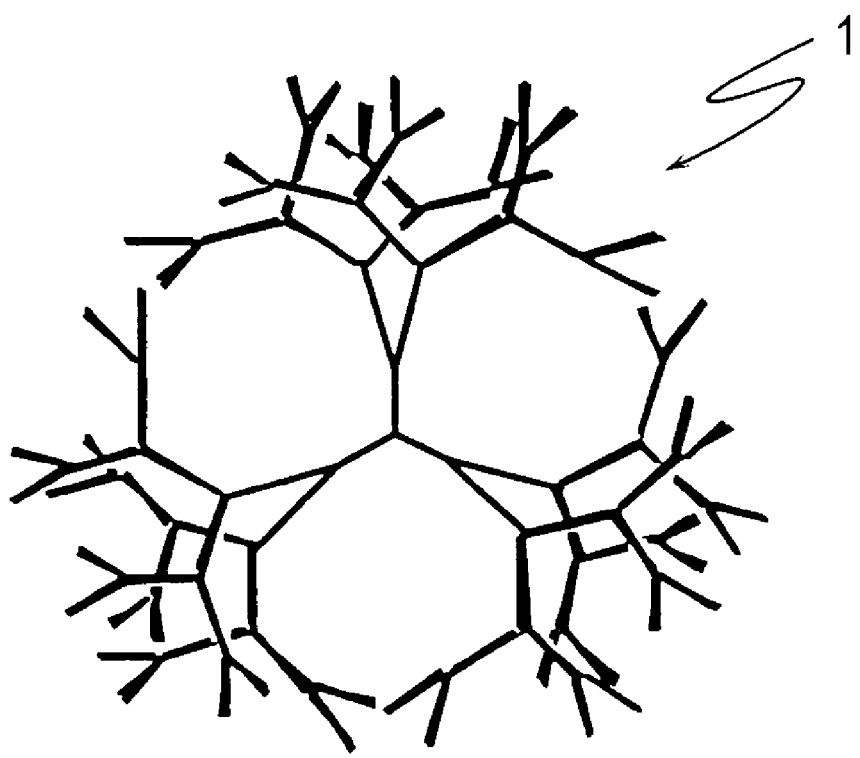
FIG. 1 shows a schematic view of a dendrimer.
Figure 2:
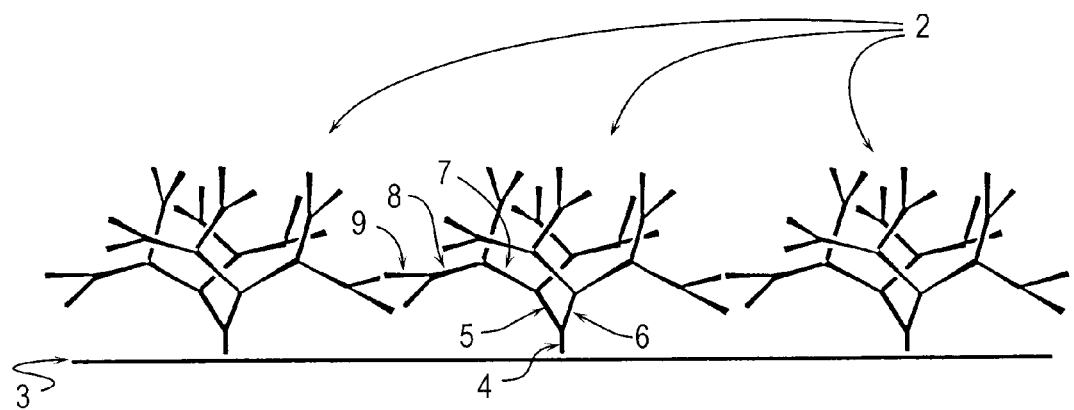
FIG. 2 shows a schematic view of dendrons attached to a surface.
Figure 3A:
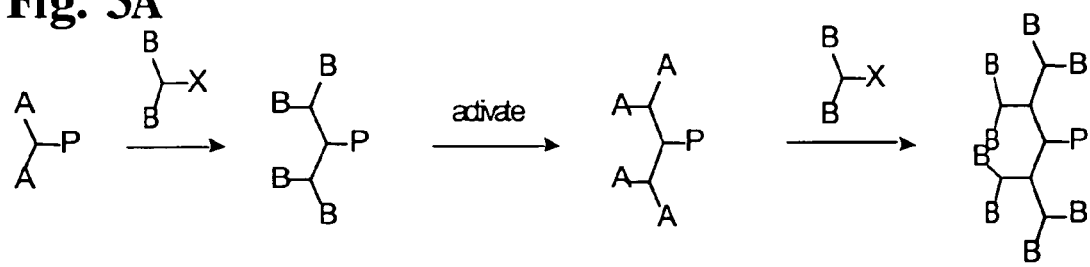
FIGS. 3A and 3B schematically illustrate methods of synthesising dendrons.
Figure 3B:
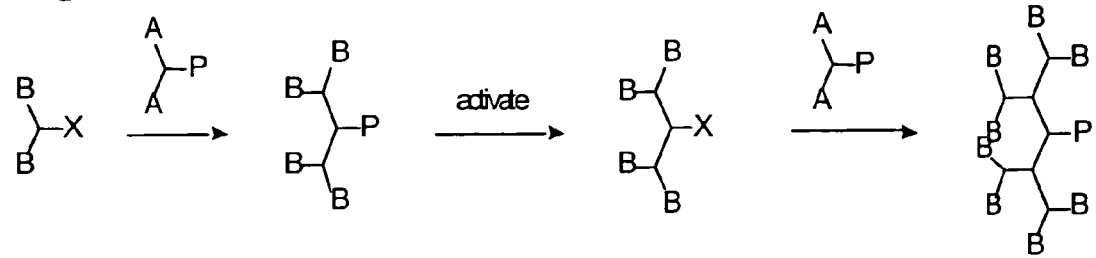

It is known to synthesise dendrons in two ways, which are illustrated schematically in FIGS. 3A and 3B respectively. In particular, FIG. 3A shows the divergent method and FIG. 3B shows Fréchet's convergent method. In both figures, A and X represent reactive groups; B and P represent unreactive groups; and P is the focal point of the dendron.

In the divergent method, the molecule is built up from the inside. In Fréchet's convergent method the molecule is synthesised from the outside. One problem associated with the divergent method is that as the dendron generation increases, the number of reactive centres increases. Therefore, the number of reactions involved in one step increases exponentially. If incomplete reaction occurs, then the number of impurities increases. Moreover, the consistency of the structure and molecular weight of the SAM molecules cannot be easily vouchsafed. In the case of the convergent method, since the number of reactive centres remains constant as the dendron generation increases, this problem is avoided. Accordingly, dendrons according to the present invention have been fabricated using Fréchet's convergent method. However, the present invention is not limited to using Fréchet's convergent method and improved performance using the divergent method can be expected.

In particular, dendron thiols with fluorinated side-chains have been produced by the inventors. More especially, fluorinated dendron thiols of various generations have been produced. That is to say, fluorinated dendron thiols have been produced using different numbers of process steps, so that dendron thiols with different numbers of "layers" of branches have been produced. However, the present invention is not limited to dendron thiols and applies equally to fluorinated dendrons with other focal points. These include, for example, dendron silanes with fluorinated side chains, in particular (but not only) where the material of the substrate on which the SAM is to be formed is glass or a silicon type material.

Ellipsometry and contact angle measurements of the formed fluorinated dendron SAMs clearly illustrates that the monolayers are highly hydrophobic and that the hydrophobicities increase with dendron generation, the number of $CF_2$ units per alkyl chain and number of perfluoroalkyl chains per branch. Moreover, the lipophobicities of the SAMs compare favourably with those of the known linear perfluoroalkyl SAMs discussed above.

All the fluorinated dendron SAMs produced by the inventors in accordance with the present invention show high good ellipsometry thickness and high hydrophobicity. However, the inventors have established that the structure of the monolayer is solvent dependent and that monolayers formed in, for example, octafluorotoluene are thinner and have lower contact angle measurements than monolayers formed in $CO_2$. In particular, the inventors have shown that monolayers formed in $CO_2$ have remarkable properties with increased hydrophobicities and thermal and chemical stabilities.

Fluorinated dendrons fabricated in accordance with the present invention include fluorinated dendron thiol examples 1 to 7 below.

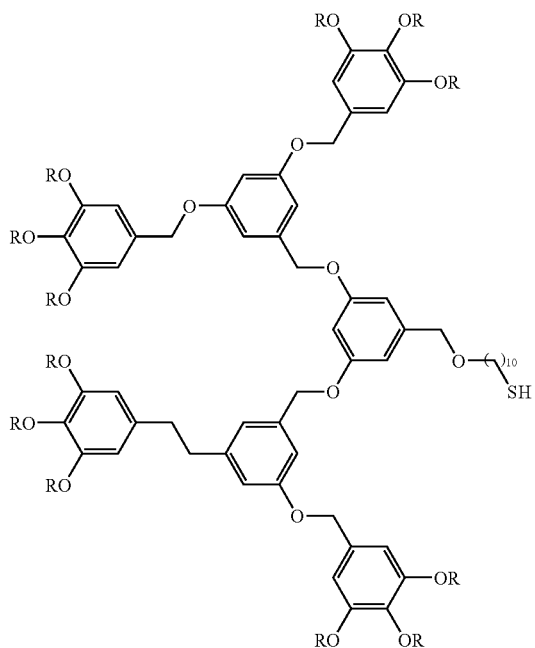

-continued

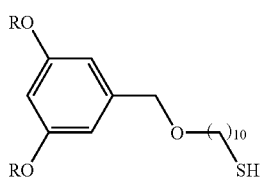

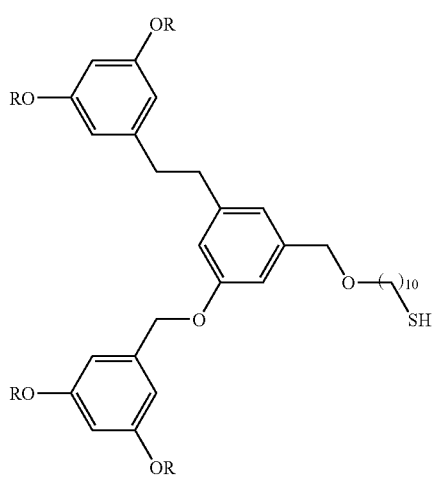

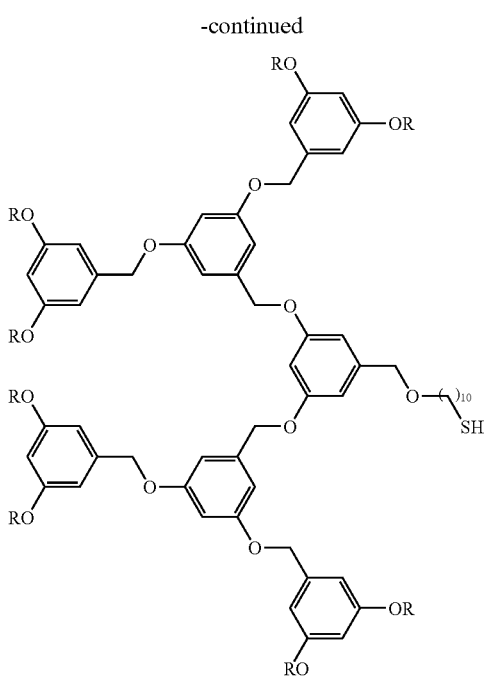

In examples 1 to 6 R=CF$_3$(CF$_2$)$_5$(CH$_2$)$_4$ and in example 7 R=CF$_3$(CF$_2$)$_9$(CH$_2$)$_4$. It can be seen that examples 1, 4 and 7 are first generation dendrons and include only a single branch terminated by a cyclic ring with varying numbers of perfluoroalkyl (RO) end chains per branch. Moreover the number of CF$_2$ units per alkyl chain in example 7 differs from the other examples. It is noted that the number of CF$_2$ units per alkyl chain is the only difference between examples 4 and 7.

A general methodology used for producing fluorinated dendron thiol examples 1 to 7 above is now discussed. This methodology is only one of many that will be apparent to those skilled in the art and should not be construed as limiting the scope of the present invention.

The first step in the fabrication of each of examples fluorinated dendrons 1 to 7 was the synthesis of the semi-fluorinated side chains for the end groups of the dendron, although a different order of steps can be carried out as desired. Scheme 1 outlines the synthetic method elaborated for the preparation of H, 1H, 2H, 2H, 3H, 3H, 4H, 4H-perfluorodecyl bromide 15 and 1H, 1H, 2H, 2H, 3H, 3H, 4H, 4H-perfluorotetradecyl bromide 16. A key step is the radical addition of a perfluoroalkyl iodide 8 and 9 to a functionalised olefin 10. Various methods of introducing perfluorinated segments of different lengths into aliphatic organic molecules are well known to persons skilled in the art. Preferably a method involving accessible and inexpensive starting materials and which can be adapted without difficulty to the preparation of other functionalised semi-fluorinated compounds is chosen.

Compound 15 was prepared by radical addition of n-perfluorohexyl iodide 8 to vinylacetic acid 10 using AIBN as the initiator. The reduction of the iodo and carboxylic groups of 11 was carried out in one step with LiAlH$_4$ to yield 13 in 51% yield over two steps. The alcohol 13 was brominated with HBr in the presence of Aliquat® 336 as phase transfer catalyst to yield the bromide 15 in 97% yield. Compound 16 was prepared using the same route; however, a lower yield of 25% was obtained in the initial radical addition/reduction steps.

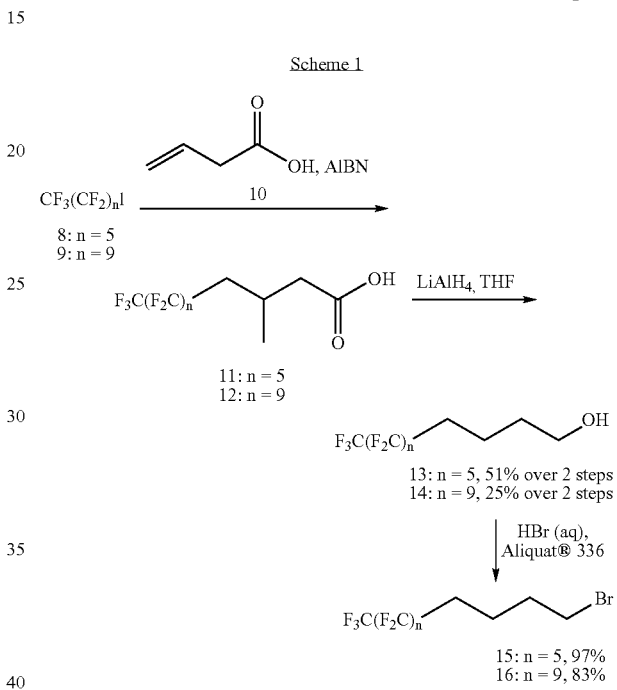

Next, the synthesis of the first generation dendron thiol examples 1 and 4 was performed, as outlined in Scheme 2, below. Methyl 3,4,5-trihydroxybenzoate 17 and methyl 3,5-dihydroxybenzoate 18 were protected using allyl bromide in DMF at 60° C. using K$_2$CO$_3$ as a base. This afforded the protected methyl esters in yields of 83% and 98% respectively. The allyl group was chosen as the protecting group owing to its ease of attachment, stability over the required functional group manipulations, and ease of removal.

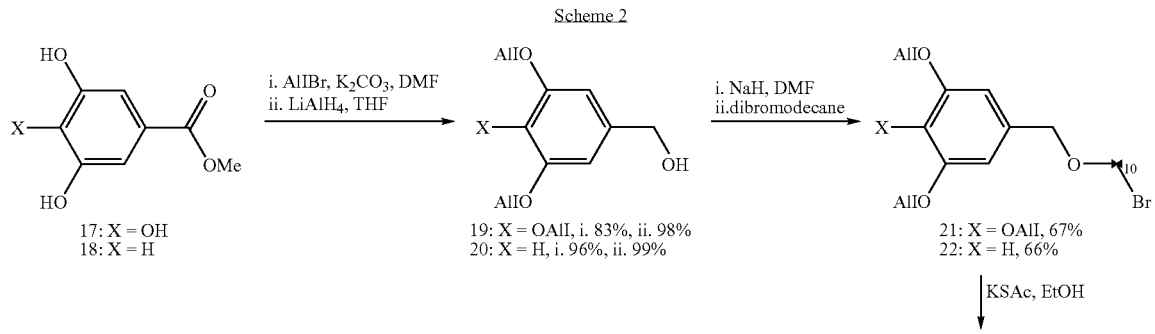

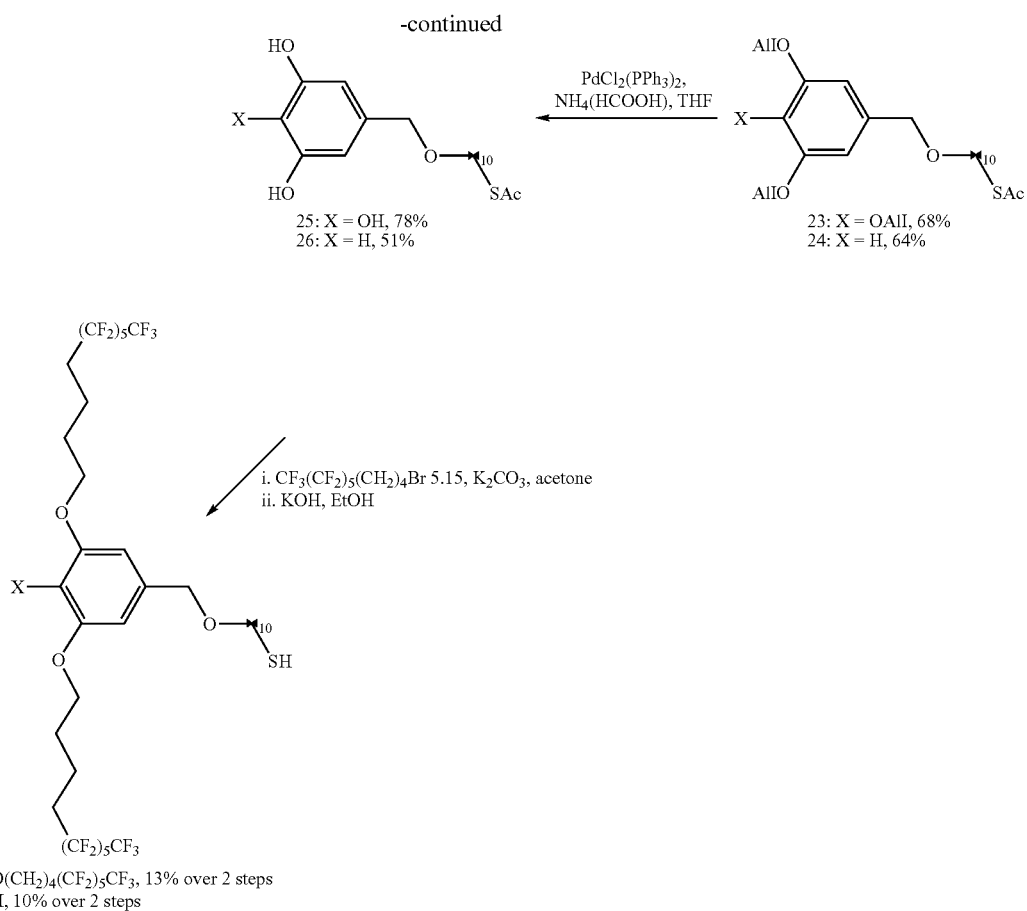

Reduction of the methyl esters using LiAlH$_4$ provided alcohols 19 and 20 in good yields of 96% and 99% respectively. The next step involved the formation of the ethers 21 and 22 by the alkylation of the alkoxides with dibromodecane followed by nucleophilic addition of thioacetate to allow the introduction of the thiol focal point, giving thioacetates 23 and 24 in good yield. The thiol focal point was introduced in a stepwise manner as shown. Finally, the removal of the allyl protecting groups from 23 and 24 using a palladium catalyst to isomerise the allyl group to an enol ether followed by acid hydrolysis occurred successfully to yield the common intermediates 25 and 26.

The final steps in the synthesis of the first generation dendrons (Scheme 2) involved alkylation of phenolate anions derived from 25 and 26 followed by deprotection of the thiol group. Alkylation of thioacetates 25 and 26 with perfluorobromide 15 in refluxing acetone containing K$_2$CO$_3$ gave the esters in low yield. This is considered to be due to either the suppression of reactivity of the bromoalkane by the electron withdrawing fluorine atoms, as schematically illustrated in FIG. 3 and/or the unwanted premature cleavage of the thioester of the thiol derivative under the basic conditions. Acetone was chosen in preference to DMF as a solvent, as DMF gave a large number of side products as observed by TLC, most probably because of the more basic conditions provided by DMF as a result of deprotection of the thiol group. Since the final step in Scheme 2 involves a deprotection, it might be thought that deprotection during this alkylation step would be acceptable. However, once the thiol is revealed, it can react with the fluorinated bromide 15 to form a thioether. Therefore, it should preferably remain protected during the penultimate alkylation step. The final step involving the deprotection of the thiol derivatives under basic conditions provided the first generation dendron thiols 1 and 4. The basic conditions required short reaction times of approximately 10 min at room temperature. This method was preferred to acidic conditions, which require refluxing for over 12 h. It has been reported that basic conditions give disulphide side products but this was not observed in this case.

The synthesis of the first generation dendron thiol example 7 with a longer fluorinated side chain as a comparison with dendron thiol example 4 is shown in Scheme 3. The synthetic route was very similar to that previously described. Alkylation of the common intermediate 26 followed by deprotection of the thiol gave dendron thiol 7 in a yield of 10%. The alkylation step was poor yielding as explained previously. In this case, acid deprotection of the intermediate thioacetate was attempted as a comparison. This provided the thiol 7 in higher yields as observed by TLC. Subsequently, deprotection under acidic conditions has been performed for larger generation dendrons.

Scheme 3

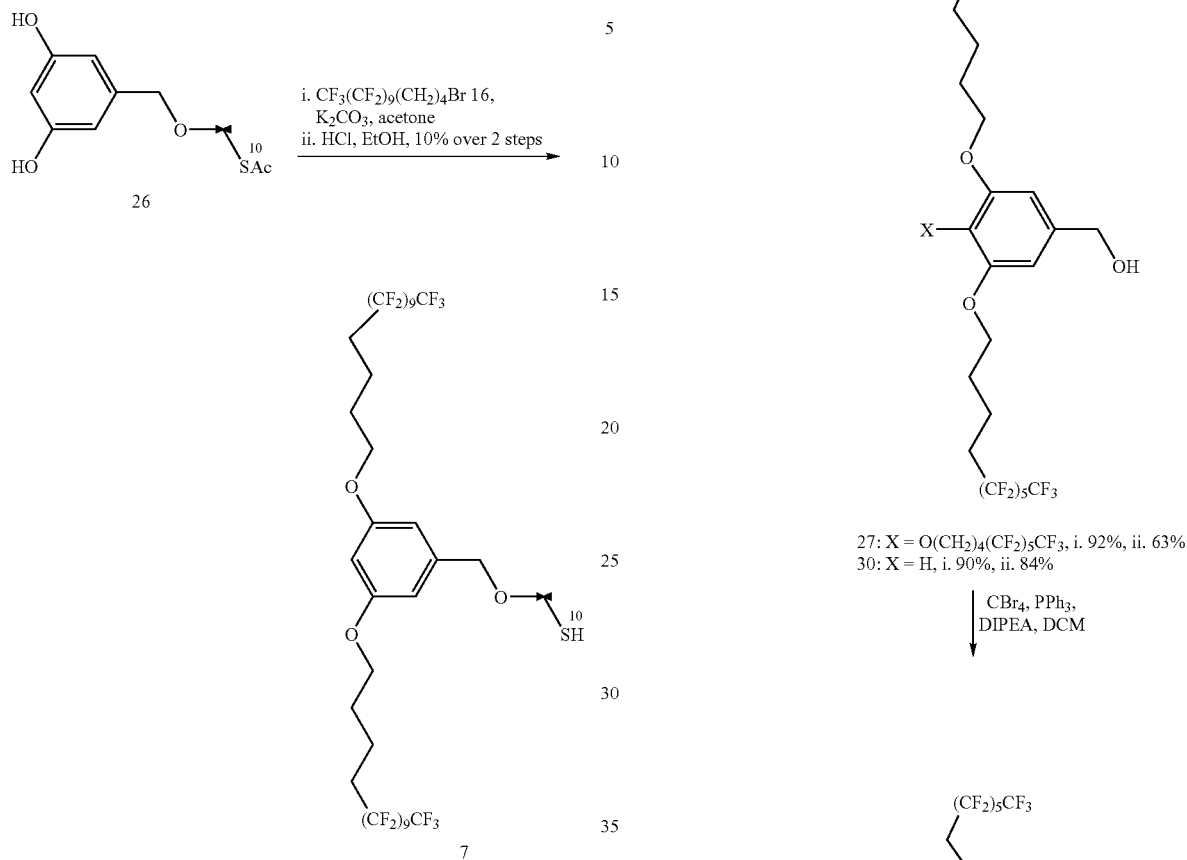

Next, the synthesis of the second and third generation dendron thiol examples 2, 3, 5 and 6 was performed. In order to use the common intermediate 26, while at the same time keeping to the convergent dendron synthesis methodology as much as possible, the first generation dendron bromides 31 and 32, were synthesised as shown in Scheme 4.

Methyl 3,4,5-trihydroxybenzoate 17 and methyl 3,5-dihydroxybenzoate 18 were alkylated with 1H, 1H, 2H, 2H, 3H, 3H, 4H, 4H-perfluorodecyl bromide 15 in DMF at 65° C. with $K_2CO_3$ as a base. Subsequent reduction using $LiAlH_4$ afforded the benzyl alcohols 27 and 30 in excellent yields. Bromination using $CBr_4$ and $PPh_3$ in the presence of DIPEA in dichloromethane provided the first generation dendron bromides 31 and 32 as required.

Scheme 4

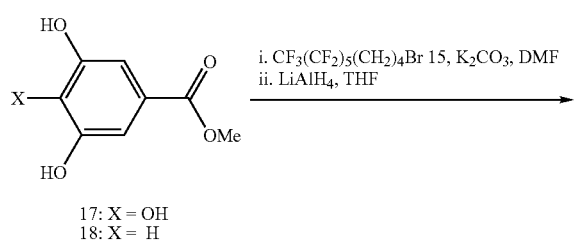

17: X = OH
18: X = H i. $CF_3(CF_2)_5(CH_2)_4Br$ 15, $K_2CO_3$, DMF
ii. $LiAlH_4$, THF

Similarly, the second generation dendron bromides 36 and 37 were synthesised as shown in Scheme 5. Alkylation of 3,5-dihydroxybenzyl alcohol 33 with bromides 31 and 32 followed by bromination yielded the second generation bromides 36 and 37 in moderate yields. Acetone was chosen as the solvent for alkylation instead of DMF due to its ease of removal.

Scheme 5

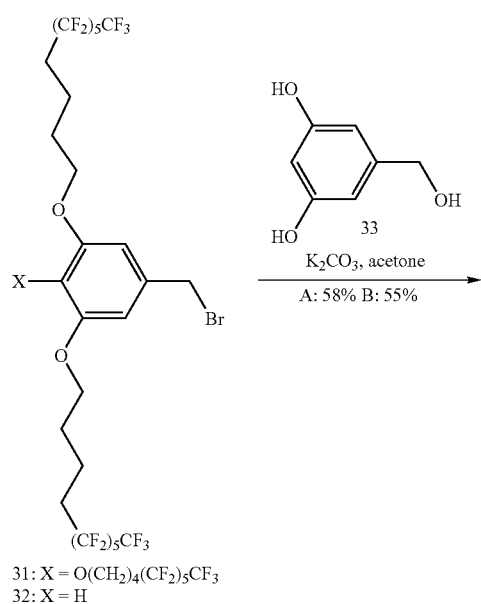

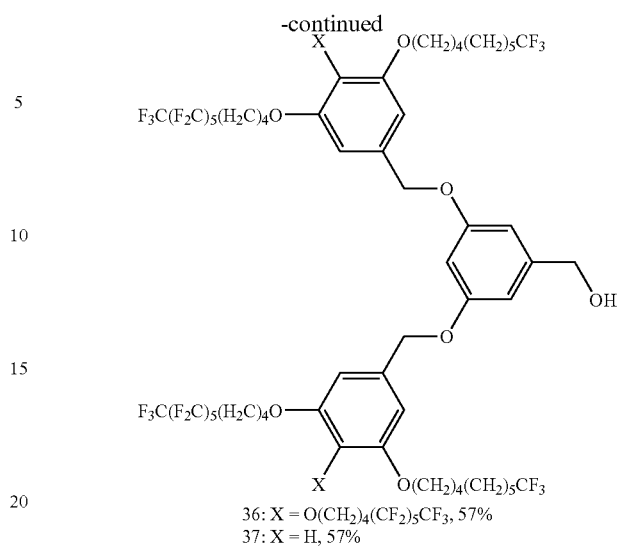

The final steps in the synthesis of the dendron thiol examples 2, 3, 5 and 6 involved the coupling of the intermediate 26 with the appropriate benzyl bromides. Scheme 6 shows the last stages in the preparation of second generation dendron thiols 2 and 5. Alkylation followed by acid deprotection afforded the thiols 2 and 5 in 10% and 12% respectively.

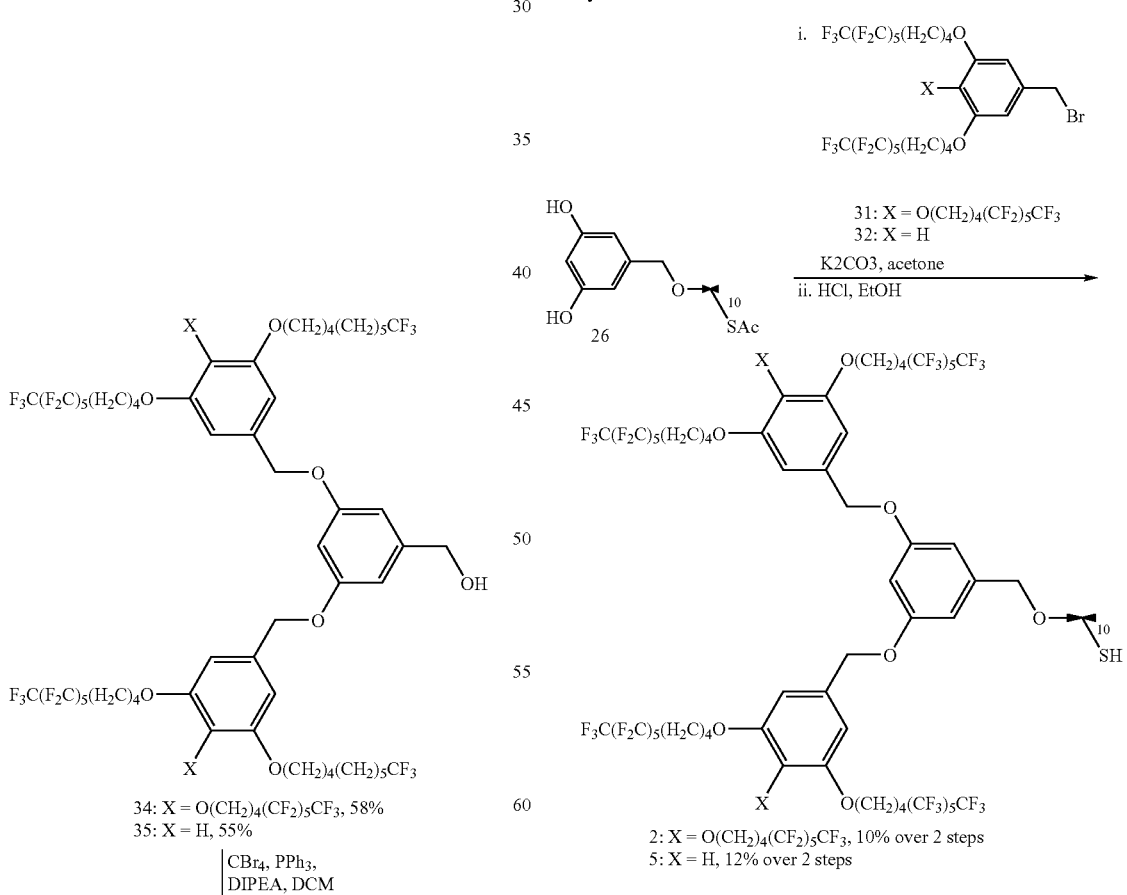

Scheme 7 shows the final stages in the synthesis of the third generation thiols 3 and 6. The same reagents as before were used in these steps. The alkylation steps involved gave higher yields.

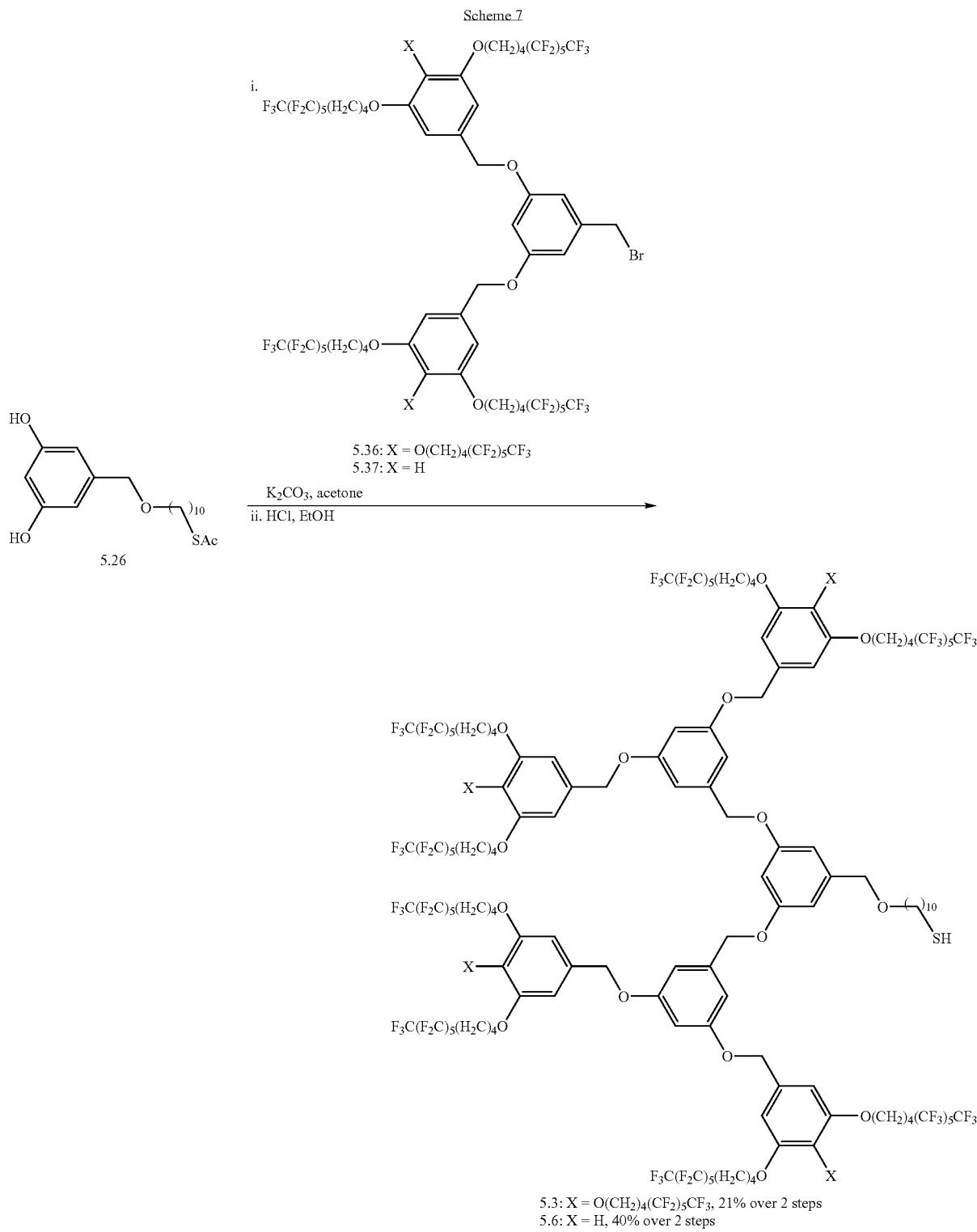

A series of fluorinated dendrons, including fluorinated dendron thiol examples 1 to 7, has been synthesised for the first time. Moreover, from the foregoing, it is clear that the inventors of the present invention have developed a successful methodology for the production of first, second and third generation fluorinated dendron thiols. This methodology could equally used for the fabrication of higher generation fluorinated dendron thiols. Moreover, it will be clear to persons skilled in the art that other fluorinated dendrons, such as fluorinated dendron silanes and fluorinated dendron thiols with different numbers of end chains and different numbers of $CF_2$ units per end chain, could also be produced using similar methodology.

In another aspect of the present invention, fluorinated dendrons are used to form SAMs on substrates. In one embodiment, fluorinated dendron thiols such as dendron thiol examples 1 to 7 are used to form SAMs on metallic substrates, such as gold substrates.

Preferably, the SAMs are formed by exposing the substrate to a solution of the fluorinated dendron in dichloromethane, a perfluorinated aromatic solvent such as octafluorotoluene, or compressed carbon dioxide. In particular, these solvents have been used for the chemisorption of dendron thiol examples 1 to 7 on metal substrates, particularly gold substrates, to form respective SAMs. However, fluorinated dendron silanes could equally well be chemisorbed on glass and silicon type substrates. The chemisorption of fluorinated dendrons on ITO also falls within the scope of the present invention.

Preferably, the substrate is exposed to the solution of fluorinated dendron and on removal from the solution and cleaned with the same solvent as used in the solution or another solvent. Subsequently, it is preferably dried in a stream of $N_2$ or other inert gas. From ellipsometry and water contact angle measurements taken from a minimum of three samples at five different regions on the same sample formed using a solution with dichloromethane as the solvent, it has been established that preferably the solution has a concentration of approximately 1 mM or more.

Preferably, the SAMs are formed at a temperature between approximately 0° C. and 40° C. It is observed that maximum advancing water contact angles occur at approximately 25° C. and that maximum ellipsometry thickness is observed at approximately 10° C. Accordingly, the SAMs are more preferably formed at a temperature between approximately 10° C. and approximately 25° C.

The variation in ellipsometry thicknesses with respect to the time of deposition of the dendron thiol examples 4 to 7 has also been observed. The gold surfaces were placed in 1 mM solutions in dichloromethane of the appropriate thiols for 10, 30, 60 and 120 min. The surfaces were rinsed with dichloromethane on removal from the dendron solutions and dried in a stream of $N_2$. It was expected that larger dendrons might show slower kinetics as this has previously been observed with chain length dependent kinetics when forming SAMs of $CH_3(CH_2)_{n-1}SH$ (n=8, 12, 16 and 18) in ethanol. However, surprisingly ellipsometry thicknesses reach a maximum value after 30 min, regardless of the size of the dendron, showing that rapid adsorption takes place is complete after 30 min. Accordingly, SAMs of the fluorinated dendrons of the present invention are preferably formed by immersion in the SAM solution for 30 minutes or less. This is considerably shorter than several hours or days, which is required for the deposition of prior art linear perfluoroalkyl SAMs.

The advancing and receding water contact angles of monolayers on gold of dendron examples 1 to 6 have been measured. The monolayers were formed by placing gold surfaces in a 1 mM solution of the appropriate dendron at room temperature for 1 h. Advancing/receding contact angles ($\theta_a/\theta_r$) of 112°/103°, 116°/103°, 118°/105°, 109°/101°, 113°/104° and 114°/106° were obtained for the monolayers of dendrons 1, 2, 3, 4, 5 and 6 respectively. A comparison between the dendron series 1 to 3, having three end chains per end branch, and dendron series 4 to 6, having two end chains per end branch, shows that the hydrophobicity of the monolayers exhibits a slight increase with dendron generation and also that the hydrophobicity increases with the number of perfluoroalkyl chains per dendritic branch.

Similarly, the variation in advancing and receding water contact angle with respect to the length of the perfluoroalkyl chain on the dendron has been measured by comparing the contact angles between surfaces formed using dendron examples 4 and 7. The contact angles are considerably higher for monolayers formed using dendron 7 (119°/110° for $\theta_a/\theta_r$) compared with monolayers formed using dendron 4 (109°/101°).

As mentioned previously, the SAMs are preferably formed by exposing the substrate to a solution of the fluorinated dendron in dichloromethane; a perfluorinated aromatic solvent such as octafluorotoluene; a combination of these two solvents; or compressed carbon dioxide, particularly supercritical carbon dioxide ($scCO_2$).

It might be expected that fluorinated dendrons would be more soluble in a fluorinated solvent, such as octafluorotoluene, than in dichloromethane. However, where a combination of dichloromethane and octafluorotoluene is used as a solvent, improved results for both contact angle and ellipsometry thickness are obtained with increasing concentration of dichloromethane. Accordingly, dichloromethane is used in preference to a perfluorinated aromatic solvent.

As discussed above, compressed carbon dioxide ($CO_2$) is known to be a clean and versatile solvent medium for a wide range of materials and, in common with fluorinated solvents such as octafluorotoluene, is known as a solvent for heavily fluorinated compounds. Accordingly, it is to be expected that compressed carbon dioxide ($CO_2$) will show similar properties to fluorinated solvents such as octafluorotoluene when used in the formation of SAMs of fluorinated dendrons. In particular, it is to be expected that monolayers formed in $CO_2$ would show similar properties to those formed in octafluorotoluene.

Nonetheless, for the purposes of experiment, gold surfaces were placed into a 10 cm³ $CO_2$ vessel along with the dendron thiol examples 1 to 7 (0.01 mmol). The vessel was sealed and connected to a $CO_2$ line. Liquid $CO_2$ was passed into the vessel, the temperature was raised to 40° C., and the pressure was adjusted by the further addition of $CO_2$ until a pressure of 1000 psi was obtained. After 1 hour, the pressure of the vessel was released and the vessel was refilled with $CO_2$. The cycle of discharging and refilling the vessel with $CO_2$ was repeated three times to ensure the surfaces were cleaned of any excess physisorbed dendrons. $\theta_a/\theta_r$ values of 120°/111°, 123°/102°, 126°/114°, 117°/114°, 120°/115° and 123°/116° were obtained for monolayers prepared using dendrons 1, 2, 3, 4, 5 and 6 respectively. These results show that monolayers formed in $CO_2$ have significantly greater hydrophobicities than those formed in dichloromethane. This was an unexpected result since monolayers formed in octafluorotoluene had shown decreased hydrophobicities.

Again, the hydrophobicity of the monolayers formed with $CO_2$ exhibits a slight increase with dendron generation. The hydrophobicity of the monolayers formed with $CO_2$ also increases with the number of perfluoroalkyl chains per dendritic branch and with the length of the perfluoroalkyl chain on the dendron.

Finally, the ellipsometric thicknesses of the monolayers of dendron thiol examples 1 to 7 formed in $CO_2$ under the conditions described above are shown in Table 1. For comparison, the ellipsometric thicknesses of the monolayers of dendron thiol examples 1 to 7 formed in dichloromethane and octafluorotoluene by exposure of the gold substrate to the solution for 1 hour are also shown in Table 1. The monolayers formed in $CO_2$ have greater thicknesses than those formed in dichloromethane, in agreement with the results of the contact angle measurements.

The theoretical value of the extended length of the dendrons is also included as a comparison. The theoretical value was obtained by performing MM2 optimisation calculations on the molecules. These results suggest that, for the monolayers formed in dichloromethane and octafluorotoluene, the dendrons are not fully extended whereas the monolayers formed in $CO_2$ are fully extended and more tightly packed. The changes in ellipsometry thicknesses are matched by the changes in contact angles.

TABLE 1

|  | Example | | |
| --- | --- | --- | --- |
|  | 1 | 2 | 3 |
| Dichloromethane | 7.6 ± 0.8 | 13.2 ± 1.1 | 20.1 ± 1.2 |
| $CO_2$ | 22.0 ± 2.2 | 39.9 ± 11.4 | 42.3 ± 3.2 |
| Theoretical values | 33 | 39 | 45 |

|  | Example | | | |
| --- | --- | --- | --- | --- |
|  | 4 | 5 | 6 | 7 |
| Octafluorotoluene | 9.7 ± 2.3 | 10.7 ± 2.8 | 13.2 ± 1.0 | 7.0 ± 1.5 |
| Dichloromethane | 10.5 ± 1.1 | 14.0 ± 1.1 | 21.8 ± 1.7 | 20.7 ± 0.6 |
| $CO_2$ | 24.5 ± 1.9 | 38.7 ± 2.1 | 43.1 ± 4.2 | 28.6 ± 1.6 |
| Theoretical values | 32 | 45 | 46 | 39 |

Monolayers formed in octafluorotoluene show contact angles ranging between 99-106° while those formed in $CO_2$ have advancing contact angles ranging between 117-126°. In addition, the hydrophobicities of the monolayers prepared in $CO_2$ also increase with dendron generation and with an increasing number of perfluoroalkyl chains per dendritic branch as for in dichloromethane.

The reasons why the use of $CO_2$ as a solvent produces improved results in comparison with octafluorotoluene are unclear. It is posited that the dendron molecules might form a more densely packed monolayer when $CO_2$ is used. This greater packing density would presumably cause the dendrons to fully extend vertically within the monolayer. For the monolayers formed in octafluorotoluene and dichloromethane, the dendrons are thought to be more loosely packed, which allows the branches of the dendrons to spread horizontally over the surface.

It is further posited that octafluorotoluene might show greater interactions with the fluorinated dendrons and disturb the inter-chain interactions within the monolayer. However, this does not explain the monolayer formation in $CO_2$. The dielectric constant for $CO_2$ is similar to that of octafluorotoluene whereas the dielectric constant for dichloromethane is considerably higher. One would thus expect that the monolayer formed in $CO_2$ would show similar properties to the monolayer formed in octafluorotoluene.

The difference in structure of the monolayer could arise because $CO_2$ is considerably smaller in size compared with octafluorotoluene, therefore causing less disruption to the inter-chain interactions. However, these results are surprising and the precise mechanisms at work are not understood. In particular, the use of $CO_2$ as a solvent has not hitherto been known to improve the properties of linear perfluoroalkyl SAMs.

If the monolayers formed with the fluorinated dendrons of the present invention are to be used for the nozzles of inkjet printers, it is important that the surfaces are lipophobic as well as being hydrophobic. Therefore, in order to assess the lipophobicity, the static contact angles of the surfaces were also measured using hexadecane instead of water.

The hexadecane contact angles of the monolayers of the present invention formed in dichloromethane and octafluorotoluene are in the range of what is expected from a linear alkyl chain SAM. Since water is a polar solvent and hexadecane is a non-polar solvent, it is expected that hexadecane will be influenced more by van der Waals interactions. As a result hexadecane is more easily influenced by the microstructure of the surface when measuring the contact angles. For example, it has been reported that the contact angle of hexadecane can be influenced by the underlying substrate due to the van der Waals interaction between itself and the substrate. The hexadecane contact angles observed for the monolayers of the present invention formed in dichloromethane and octafluorotoluene may be due to the increased disorder on the surface of these dendron monolayers.

In the case of the water contact angles, the contact angles of the monolayers formed in dichloromethane were greater than those formed in octafluorotoluene. In contrast, for the hexadecane contact angles, the values obtained for the monolayers formed in octafluorotoluene are greater than those formed in dichloromethane. This is counterintuitive and is not understood.

However, the hexadecane contact angles of the monolayers formed in $CO_2$ are large, matching the water contact angle results. Thus, they compare well with hexadecane contact angles for linear perfluoroalkyl chain SAMs, which vary between 77 and 83°. This would appear to confirm that the monolayers formed in $CO_2$ are more tightly packed than those formed in organic solvents.

For an inkjet printer nozzle to be effective, it must to be chemically and thermally robust as well as being hydrophobic. Studies were thus performed to evaluate the thermal and chemical stability of the fluorinated dendron monolayers.

In order to study the thermal stability of the dendron monolayers, the monolayers of dendron examples 4 to 7 formed in dichloromethane, octafluorotoluene and $CO_2$ were incubated for 1 hour in an oven at 150° C. After incubation, the surfaces were allowed to cool to room temperature and rinsed with dichloromethane to remove any desorbed material. The surfaces were then dried under a stream of $N_2$. Finally, the monolayers were studied using ellipsometry and contact angle measurements.

Similarly, in order to study the chemical stability of the monolayers, they were heated in DMSO for 1 hour at 150° C. The surfaces were allowed to cool to room temperature, rinsed with dichloromethane and dried under a stream of $N_2$. The monolayers were then studied using ellipsometric and contact angle measurements.

The results obtained were disappointing for monolayers formed in dichloromethane and octafluorotoluene after both chemical and thermal treatments. Indeed, contrary to expectations, they were worse than those for semi-fluorinated linear alkyl SAMs of $F(CF_2)_{10}(CH_2)_n SH$ where n=2, 6, 11, 17 and 33. Thus, it would appear that the dendron monolayers are less thermally stable than the linear perfluoroalkyl SAMs.

The decrease in thermal and chemical stability could possibly be explained by the structure of the molecules within the monolayer. The stability of a SAM is understood to be greatly influenced by the van der Waals interaction between the chains within the monolayer. For a linear perfluoroalkyl SAM, the chains are well-ordered and are in the trans conformation. The chains are also tilted away from the surface normal thereby maximising the inter-chain van der Waals interactions. In contrast, there might be a disordered structure within the monolayer of dendrons since the molecules would not be able to pack as efficiently. Inter-chain van der Waals interactions would therefore be reduced along with the thermal stability of the monolayer.

In contrast, the monolayers formed in $CO_2$ proved to be more robust and the ellipsometry and contact angle results of these monolayers before and after thermal and chemical treatment are summarised in Table 2 below. After treatment, the monolayers have reduced in thickness and the water contact angles have also decreased a little showing that some degradation of the monolayer has taken place. Furthermore, the contact angle hysteresis has increased showing that there is increased disorder on the surface of the monolayer.

|  | 5.4 | 5.5 | 5.6 | 5.7 |
| --- | --- | --- | --- | --- |
| Ellipsometry thickness |  |  |  |  |
| Before/Å | 24.5 ± 1.9 | 38.7 ± 2.1 | 43.1 ± 4.2 | 28.6 ± 1.9 |
| After/Å (Thermal) | 10.7 ± 0.5 | 25.1 ± 3.6 | 26.8 ± 2.3 | 11.2 ± 1.3 |
| (Chemical) | 11.3 ± 1.7 | 7.7 ± 2.6 | 22.0 ± 5.6 | 11.0 ± 1.2 |
| Water contact angle |  |  |  |  |
| Before/° | 117/114 | 120/115 | 123/116 | 124/113 |
| After/° (Thermal) | 114/98 | 116/105 | 117/108 | 123/110 |
| (Chemical) | 93/82 | 92/86 | 92/85 | 112/101 |
| Contact angle hysteresis |  |  |  |  |
| Before/° | 0.05 | 0.08 | 0.11 | 0.17 |
| After/° (Thermal) | 0.27 | 0.18 | 0.14 | 0.20 |
| (Chemical) | 0.19 | 0.10 | 0.12 | 0.18 |

Table 2 shows the ellipsometry thickness, water contact angles and contact angle hysteresis of monolayers of dendrons 5.4-5.7 formed in $CO_2$ before and after thermal treatment. Monolayers were incubated for 1 h at 150° C. for thermal treatment. Monolayers were originally formed by the exposure of the gold surface to a 1 mM solution of the dendrons for 1 h at 40° C. and 1000 psi.

However, it is notable that although the contact angles of these SAMs have decreased a little, they still exhibit a high degree of hydrophobicity, which still compares favourably with the hydrophobicity of known linear perfluoroalkyl chain SAMs that have not undergone chemical and thermal degradation treatments.

It is speculated that the increased thickness and increased water contact angles of a monolayer in $CO_2$ are due to an increased packing density of the monolayers causing the dendrons to extend vertically to their full lengths. If this is true, then there may be increased inter-chain van der Waals interactions within the monolayers formed in $CO_2$, which would explain the increase in thermal and chemical stability. During the incubation, some of the dendrons may desorb from the surface thereby reducing the packing density of the monolayer. However, the dendrons would still be sufficiently packed to allow the dendritic branches to spread and maintain good coverage over the surface. This would explain the reduction in ellipsometry thickness and contact angle.

In contrast, it is speculated that the possible lower packing density of fluorinated dendritic SAMs formed using dichloromethane and octafluorotoluene reduces the inter-chain van der Waals interactions within the monolayers formed in $CO_2$. This would lead to reduced stability. Moreover, each dendron comprises a large number of dendritic branches and a single attachment site, be it a thiol, a silane or another attachment site. Accordingly, if the dendrons are not tightly packed, the dendritic branches are able to spread horizontally—that is, parallel to the surface of the substrate. Consequently, when a dendron is removed a comparatively large surface area of the substrate is uncovered. Moreover, since the dendritic branches are already spread, they are unable to spread further to cover the gap.

Returning to fluorinated dendritic SAMs formed using $CO_2$, it is suggested that during the incubation some of the dendrons may desorb from the surface thereby reducing the packing density of the monolayer. However, the dendrons would still be sufficiently packed to allow the dendritic branches to spread and maintain good coverage over the surface of the substrate. This would explain the considerably smaller reduction in ellipsometry thickness and contact angle.

In summary, the inventors of the present invention have realised that a high degree of hydrophobicity can be achieved by forming a SAM of dendrons with fluorinated side-chains, which are hitherto unknown.

Accordingly, the inventors have produced a variety of such fluorinated dendrons and have further produced SAMs under different conditions using this variety of fluorinated dendrons. Specifically, the SAMs were produced under a variety of temperatures and using a variety of solvents. In each case, it has been found that a surface with an unexpectedly high hydrophobicity is produced. Moreover, the deposition time using dichloromethane and octafluorotoluene as solvents is significantly reduced compared with the prior art. Consequently, these SAMs can usefully be used for a variety of applications where hydrophobicity is desired but high degrees of chemical and thermal stability are not required. Such applications include self-cleaning and anti-fogging windows, mirrors and visors and snow or rain drop repelling surfaces. Of course, such applications and devices included in and for such applications form part of the present invention.

Moreover, in some embodiments the SAMs have unexpectedly high and hitherto unknown degrees of not only hydrophobicity but also chemical and thermal stability. This is evidenced by the high contact angles of water on the SAMs and by the ellipsometry thickness of the SAMs, even after chemical and thermal treatment. Such SAMs are suited to general applications where hydrophobicity is desired, as well as more particular applications where a degree of chemical and thermal stability is required.

Such applications include ensuring the hydrophobicity of the nozzle of an inkjet printer in order to ensure that the nozzle does not become clogged but is instead self-cleaning. By this is meant that ink passing through the nozzle is repelled by the nozzle surface and that the surface tension of the ink ensures that impurities already deposited on the nozzle are swept out with the ink. This ensures high resolution of the inkjet printer. This is particularly important for printing of photographic images and electrical circuits and devices, such as transistors, which require the deposition of droplets of ink or other solution of the order of picolitres.

The hydrophobicities of the fluorinated dendrons increase with dendron generation, the number of $CF_2$ units per alkyl chain and the number of perfluoroalkyl chains per branch. The fluorinated dendritic monolayers formed in $CO_2$ show remarkable properties with increased hydrophobicities and thermal and chemical stabilities.

The present invention includes any device comprising a self-assembled monolayer formed of fluorinated dendrons, in particular any device comprising a fluorinated dendritic monolayer formed in $CO_2$ and any fluid deposition device, such as an ink jet printer, comprising such a monolayer.

The foregoing description discusses SAMs with a silane or, in particular, a thiol at the focal point. However, it should be understood that other suitable anchoring moieties can also be used. These include phosphonates and carboxylic acids.

The foregoing description has been given by way of example only and it will be appreciated by a person skilled in the art that modifications can be made without departing from the scope of the present invention.

The invention claimed is:

1. A dendron comprising a focal point and a plurality of fluorinated end groups;
wherein the dendron is selected from the group consisting of compounds represented by formulas 1 though 7:

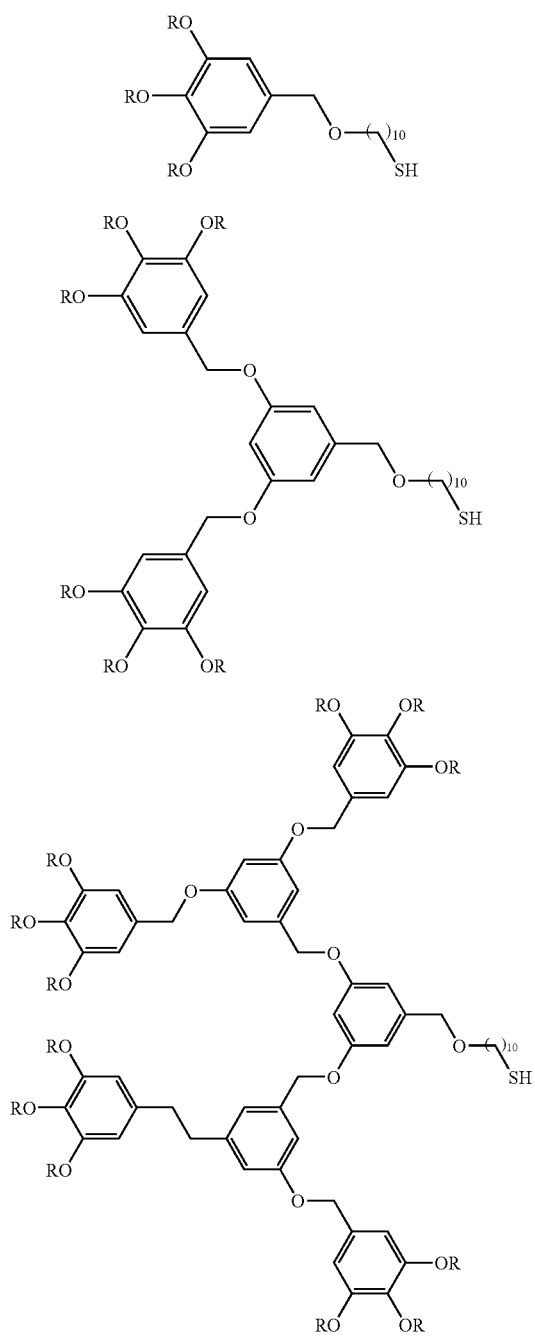

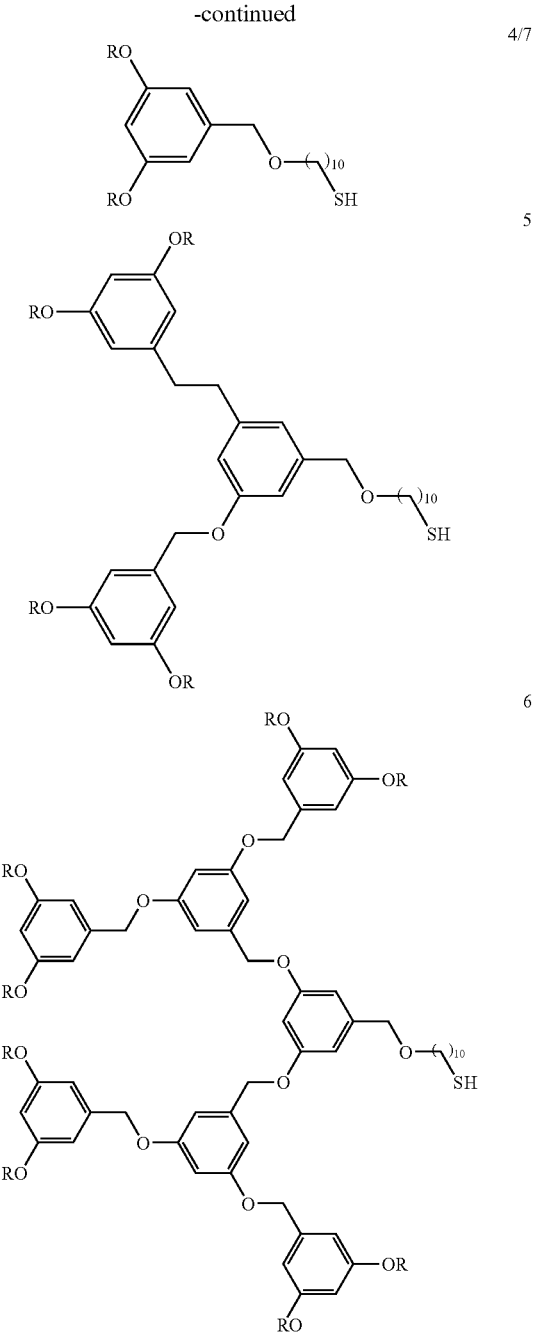

where in formulas 1 to 6 R=$CF_3(CF_2)_5(CH_2)_4$ and in formula 7 R=$CF_3(CF_2)_9(CH_2)_4$.

2. A dendron according to claim 1, wherein the dendron is a first generation dendron.

3. A dendron according to claim 2, having the structure of formula 1.

4. A dendron according to claim 2, having the structure of formula 4.

5. A dendron according to claim 2, having the structure of formula 7.

6. A dendron according to claim 1, wherein the dendron is a second generation dendron.

7. A dendron according to claim 6, having the structure of formula 2.

8. A dendron according to claim 6, having the structure of formula 5.

9. A dendron according to claim 1, wherein the dendron is a third or more generation dendron.

10. A dendron according to claim 9, having the structure of formula 3.

11. A dendron according to claim 9, having the structure of formula 6.

12. A self-assembled monolayer comprising a plurality of dendrons according to claim 1 bonded to a substrate.

13. A self-assembled monolayer according to claim 12, wherein the substrate is a metal and the plurality of dendrons includes dendrons having a thiol as the focal point.

14. A self-assembled monolayer according to claim 13, wherein the monolayer is formed by exposure of the substrate to a solution of the dendron in dichloromethane and/or octafluorotoluene.

15. A self-assembled monolayer according to claim 14, wherein the concentration of the dendron in the solution is approximately 1 mM or more.

16. A self-assembled monolayer according to claim 14, wherein substrate is exposed to the solution at a temperature of between approximately 10° C. and 65° C.

17. A self-assembled monolayer according to claim 14, wherein substrate is exposed to the solution at a temperature of between approximately 10° C. and 25° C.

18. A self-assembled monolayer according to claim 14, wherein the substrate is exposed to the solution for between approximately 1 minute and 24 hours.

19. A self-assembled monolayer according to claim 14, wherein the substrate is exposed to the solution for approximately 30 minutes or less.

20. A self-assembled monolayer according to claim 13, wherein the monolayer is formed by exposure of the substrate to the dendron in compressed $CO_2$.

21. A self-assembled monolayer according to claim 20, wherein the $CO_2$ is supercritical $CO_2$.

22. A self-assembled monolayer according to claim 20, wherein the monolayer is formed by placing the substrate surface and the dendron in a sealed vessel, introducing $CO_2$ and discharging the $CO_2$ from the vessel.

23. A self-assembled monolayer according to claim 22, wherein the $CO_2$ is introduced at a pressure of up to 1000 psi.

24. A self-assembled monolayer according to claim 22, wherein the steps of placing the substrate surface and the dendron in a sealed vessel, introducing $CO_2$ up to a pressure of 1000 psi and discharging the $CO_2$ from the vessel are repeated three or more times.

25. A device comprising a self-assembled monolayer according to claim 12.

26. A device according to claim 25, wherein the device is a fluid deposition device.

27. A device according to claim 26, wherein the device is an ink jet print head or an ink jet printer.

* * * * *